(12) United States Patent
Qi

(10) Patent No.: US 9,629,539 B2
(45) Date of Patent: Apr. 25, 2017

(54) EYEGLASSES-WEARING SIMULATION METHOD, PROGRAM, DEVICE, EYEGLASS LENS-ORDERING SYSTEM AND EYEGLASS LENS MANUFACTURING METHOD

(71) Applicant: HOYA CORPORATION, Tokyo (JP)

(72) Inventor: Hua Qi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/186,926

(22) Filed: Feb. 21, 2014

(65) Prior Publication Data

US 2014/0168607 A1    Jun. 19, 2014

Related U.S. Application Data

(63) Continuation-in-part of application No. PCT/JP2012/071162, filed on Aug. 22, 2012.

(30) Foreign Application Priority Data

Aug. 24, 2011    (JP) .................. 2011-182208

(51) Int. Cl.
*A61B 3/09*       (2006.01)
*G02C 7/02*       (2006.01)
*A61B 3/00*       (2006.01)

(52) U.S. Cl.
CPC .............. *A61B 3/09* (2013.01); *A61B 3/0025* (2013.01); *A61B 3/0058* (2013.01); *G02C 7/028* (2013.01)

(58) Field of Classification Search
CPC ........... A61B 3/08–3/10; A61B 3/0025; G02C 7/025; G02C 7/027; G02C 7/028; G01M 11/0257; G06F 17/5009

(Continued)

(56) References Cited

U.S. PATENT DOCUMENTS 5,311,356 A * 5/1994 Freilich .................... G02C 7/02
                                                        351/159.02
6,329,989 B1   12/2001 Qi et al.
(Continued)

FOREIGN PATENT DOCUMENTS

EP    1 158 338 A2    11/2001
EP    2 341 388 A1    7/2011
(Continued)

OTHER PUBLICATIONS

International Search Report issued in International Patent Application No. PCT/JP2012/071162 mailed Sep. 18, 2012 (with translation).

(Continued)

*Primary Examiner* — Scott J Sugarman
*Assistant Examiner* — Gary O'Neill
(74) *Attorney, Agent, or Firm* — Oliff PLC

(57) ABSTRACT

An eyeglasses-wearing simulation method comprising: a step of creating a pair of left and right original images for enabling a patient to perform stereoscopic viewing by utilizing binocular parallax, based on virtual scene data constituted by virtual objects placed in visual field spaces of the left and right eyes; a step of calculating distortion and blur of a right eye eyeglass lens and adding the distortion and blur to the right eye original image, and calculating distortion and blur of a left eye eyeglass lens and adding the distortion and blur to the left eye original image; and a step of stereoscopically displaying the processed images viewed through the pair of left and right eyeglass lenses on a screen, wherein a value of the blur is calculated by setting a same amount of accommodation to the left and right eyes in regard to all of object points.

14 Claims, 9 Drawing Sheets

(58) Field of Classification Search
USPC ..... 351/237, 239, 240, 246; 345/428; 703/2, 703/6
See application file for complete search history.

(56) References Cited

U.S. PATENT DOCUMENTS

| | | | |
|---|---|---|---|
| 2001/0056338 A1* | 12/2001 | Qi | G02C 7/028 703/6 |
| 2003/0076479 A1 | 4/2003 | Qi | |
| 2008/0052194 A1* | 2/2008 | Shinohara | G02C 13/003 705/26.81 |
| 2010/0114540 A1* | 5/2010 | Shinohara | G01M 11/0257 703/1 |
| 2012/0105609 A1* | 5/2012 | Qi | 348/54 |

FOREIGN PATENT DOCUMENTS

| | | |
|---|---|---|
| JP | B2-3342423 | 11/2002 |
| JP | B2-3825654 | 9/2006 |
| JP | B2-3919097 | 5/2007 |
| JP | A-2009-230699 | 10/2009 |
| WO | WO 2010/044383 A1 | 4/2010 |

OTHER PUBLICATIONS

International Preliminary Report on Patentability issued International Patent Application No. PCT/JP2012/071162 mailed Feb. 25, 2014 (with translation).

Apr. 30, 2015 Extended European Search Report issued in European Application No. 12826151.8.

March 31, 2016 Notification of Reasons for Rejection issued in Japanese Patent Application No. 2013-530036.

Feb. 1, 2017 Examination Report issued in European Patent Application No. 12826151.8.

* cited by examiner

EYEGLASSES-WEARING SIMULATION METHOD, PROGRAM, DEVICE, EYEGLASS LENS-ORDERING SYSTEM AND EYEGLASS LENS MANUFACTURING METHOD

This is a Continuation-in-Part of International Application No. PCT/JP2012/071162 filed Aug. 22, 2012, which claims priority from Japanese Patent Application No. 2011-182208 filed Aug. 24, 2011. The entire disclosure of the prior application is hereby incorporated by reference herein its entirety.

TECHNICAL FIELD

The present invention relates to an eyeglasses-wearing simulation method, eyeglasses-wearing simulation program, an eyeglasses-wearing simulation device, an eyeglass lens-ordering system and an eyeglass lens manufacturing method for simulating how the outside is viewed when a pair of left and right eyeglass lenses are placed in front of left and right eyes.

BACKGROUND

In an eyeglass store, an eye examination is conducted for a patient, and the type of eyeglass lens is selected based on a prescription obtained by eye examination. The types of eyeglass lens include a single-vision spherical lens, a single-vision aspherical lens, a fatigue-relieving lens, a near vision lens dedicated for near vision, a progressive power lens (distance/near vision type, intermediate/near vision type). For a plurality of types of eyeglass lenses, a plurality of types of test lenses are prepared. In an eyeglass store, a test lens is inserted into a temporary frame and is put on a patient on a trial basis so that the prescribed power is achieved. Such trial wearing is an only chance for the patient to check how the outside is viewed in an eyeglass-wearing state. However, regarding trial wearing of an eyeglass lens having as specialized transmission power distribution, such as is progressive power lens, in many cases, actual visual performance in the eyeglass wearing state was not adequately reflected.

For this reason, an eyeglass-wearing simulation device which enables a patient to artificially experience how the outside is viewed in the eyeglass wearing state has been proposed. For example, Japanese Patent Publication No. 3342423 (B2) (hereafter, referred to as "patent document 1") describes an example of a specific configuration of an eyeglass-wearing simulation device.

The eyeglass-wearing simulation device described in patent document 1 simulates the visual performance in a state where an eyeglass lens is placed in front of a single eye. To achieve the precise simulation, the simulation device of this type is able to reproduce the visual performance while considering shaking, distortion and blur caused during wearing of the eyeglass while further considering perception of a human.

SUMMARY

However, a human observes the outside not by a single eye, but by both eyes. Therefore, the simulation disclosed in the patent document 1 where the visual performance by a single eye is reproduced was in adequate in regard to how a wearer perceives the outside when the wearer actually wears the eyeglasses.

In view of the above described problem, the object of the present invention is to provide an eyeglasses-wearing simulation method, an eyeglasses-wearing simulation program, an eyeglasses-wearing simulation device, an eyeglass lens-ordering system and an eyeglass manufacturing method suitable for simulating how the outside is viewed in binocular vision when a wearer wears eyeglasses.

According to an embodiment of the invention, there is provided an eyeglasses-wearing simulation method for simulating how an outside is viewed when a pair of left and right eyeglass lenses are placed in front of left and right eyes. The method comprises: an original image creation step of creating a pair of left and right original images for enabling a patient to perform stereoscopic viewing by utilizing binocular parallax, based on virtual scene data constituted by virtual objects placed in visual field spaces of the left and right eyes; an image creation step of calculating, based on optical data of a right eye eyeglass lens of the pair of left and right eyeglass lenses deigned in accordance with prescription information of the patient, distortion and blur of the right eye eyeglass lens and processing the right eye original image by adding the distortion and blur of the right eye eyeglass lens to the right eye original image, and calculating, based on optical data of a left eye eyeglass lens of the pair of left and right eyeglass lenses, distortion and blur of the left eye eyeglass lens and processing the left eye original image by adding the distortion and blur of the left eye eyeglass lens to the left eye original image, so as to create images of left and right visual fields viewed through the pair of left and right eyeglass lenses; and an image display step of stereoscopically displaying the processed images viewed through the pair of left and right eyeglass lenses on a screen. In this method, in the image creation step of creating the images of the left and right visual fields viewed through the pair of left and right eyeglass lenses, a value of the blur is calculated by setting a same amount of accommodation to the left and right eyes in regard to all of object points in the visual field spaces.

Since when the blur of each object point in the visual field space is calculated, the amount of accommodation common to the left and right eyes is set without setting optimum amounts of accommodation individually for the left and right eyes. Therefore, the patient is given the eyeglass lens-wearing simulation which reflects more accurately how the outside is viewed when the eyeglass lenses are worn, and is able to achieve the stereoscopic viewing for the parallax images in a feeling close to the reality.

The same amount of accommodation which is set in the image creation step for each object point in the visual field space may be set according the following rule A or B.

A: an amount of accommodation in a single vision of a dominant eye of the patient, for each object point in the visual field spaces.

B: a smaller one of amounts of accommodation required for the left and right eyes, for each object point in the visual field spaces.

According to another embodiment of the invention, there is provided a computer readable medium having computer readable instruction stored thereon, which, when executed by a processor of a computer, configures the processor to perform the steps of the above described eyeglasses-wearing simulation method.

According to another embodiment of the invention, there is provided an eyeglasses-wearing simulation device for simulating how an outside is viewed when a pair of left and right eyeglass lenses is placed in front of left and right eyes. The device comprises: an original image creation unit configured to create a pair of left and right original images for enabling a patient to perform stereoscopic viewing by utilizing binocular parallax, based on virtual scene data constituted by virtual objects placed in visual field spaces of the left and right eyes; an image creation unit configured to calculate, based on optical data of as right eye eyeglass lens of the pair of left and right eyeglass lenses deigned in accordance with prescription information of the patient, distortion and blur of the right eye eyeglass lens and to process the right eye original image by adding the distortion and blur of the right eye eyeglass lens to the right eye original image, and configured to calculate, based on optical data of as left eye eyeglass lens of the pair of left and right eyeglass lenses, distortion and blur of the left eye eyeglass lens and to process the left eye original image by adding the distortion and blur of the left eye eyeglass lens to the left eye original image, so as to create images of left and right visual fields viewed through the pair of left and right eyeglass lenses; and an image display unit configured to stereoscopically display the processed images viewed through the pair of left and right eyeglass lenses. In the image creation unit, a value of the blur is calculated by setting a same amount of accommodation to the left and right eyes in regard to all of object points in the visual field spaces.

According to another embodiment of the invention, there is provided an eyeglass lens ordering system for ordering a pair of eyeglass lenses using an eyeglasses-wearing simulation device for simulating how an outside is viewed when the pair of left and right eyeglass tenses is placed in front of left and right eyes, comprising: the above described eyeglasses-wearing simulation device; and an order data transmission unit configured to transmit, as ordering data, one of the prescription information used by the image creation unit of the eyeglasses-wearing simulation device and eyeglass lens pair data designed based on the prescription data to a predetermined ordering destination.

According to another embodiment of the invention, there is provided an eyeglass lens manufacturing method, comprising the steps of: an execution step of executing the above described eyeglasses-wearing simulation method; a transmission step of transmitting, as ordering data, one of the prescription information used in the image creation step in the eyeglasses-wearing simulation method and eyeglass lens pair data designed based on the prescription information, to a predetermined ordering destination; and a manufacturing step of processing lens material by driving and controlling a processing machine based on one of the transmitted prescription data and the transmitted eyeglass lens pair data designed based on the prescription information, thereby manufacturing the eyeglass lenses.

According to another embodiment of the invention, there is provided an eyeglass lens design method for designing a pair of eyeglass lenses based on prescription information of a patient, comprising the steps of: a calculation step of calculating a value of blur of the eyeglass lenses by setting a same amount of accommodation for left and right eyes in regard to all object points in visual field spaces for the left and right eyes; and a design step of designing the pair of eyeglass lenses using the calculated value of the blur. The same amount of accommodation for the left and right eyes set for all the object points in the visual field spaces may be equal to an amount of accommodation in a single vision of a dominant eye of the patient, or may be equal to a smaller one of amounts of accommodation required for the left and right eyes.

According to another embodiment of the invention, there is provided an eyeglass lens manufacturing method, comprising the steps on a design step of designing a pair of eyeglass lenses based on prescription information of a patient by calculating a value of blur of the eyeglass lenses and setting a same amount of accommodation for left and right eyes in regard to all object points in visual field spaces for the left and right eyes, and thereby designing the pair of eyeglass lenses using the calculated value of the blur; a transmission step of transmitting design data of the designed pair of eyeglass lenses, to a predetermined ordering destination; and a manufacturing step of manufacturing the eyeglass lenses by driving and controlling a processing machine, at the ordering destination, using the received design data. In this manufacturing method, the same amount of accommodation for the left and right eyes set for all the object points in the visual field spaces may be equal to an amount of accommodation in a single vision of a dominant eye of the patient, or may be equal to a smaller one of amounts of accommodation required for the left and right eyes.

DETAILED DESCRIPTION OF EMBODIMENTS

In the following, an eyeglass lens-ordering system according to an embodiment of the invention is explained with reference to the accompanying drawings.

(Eyeglass Lens-Ordering System 10)

Figure 1:
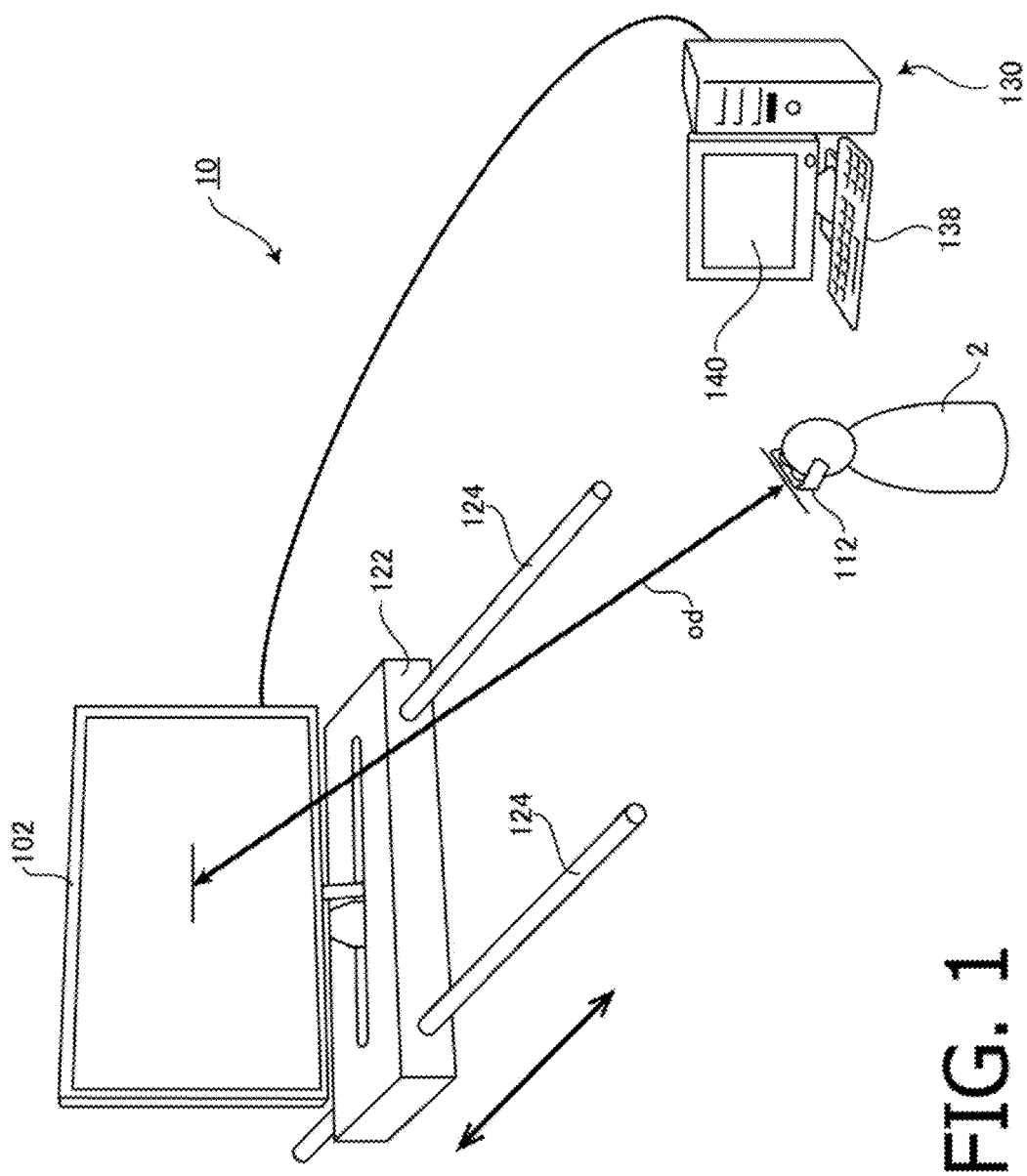
FIG. 1 is a diagram generally illustrating an eyeglass lens-ordering system according to an embodiment of the invention.
Figure 2:
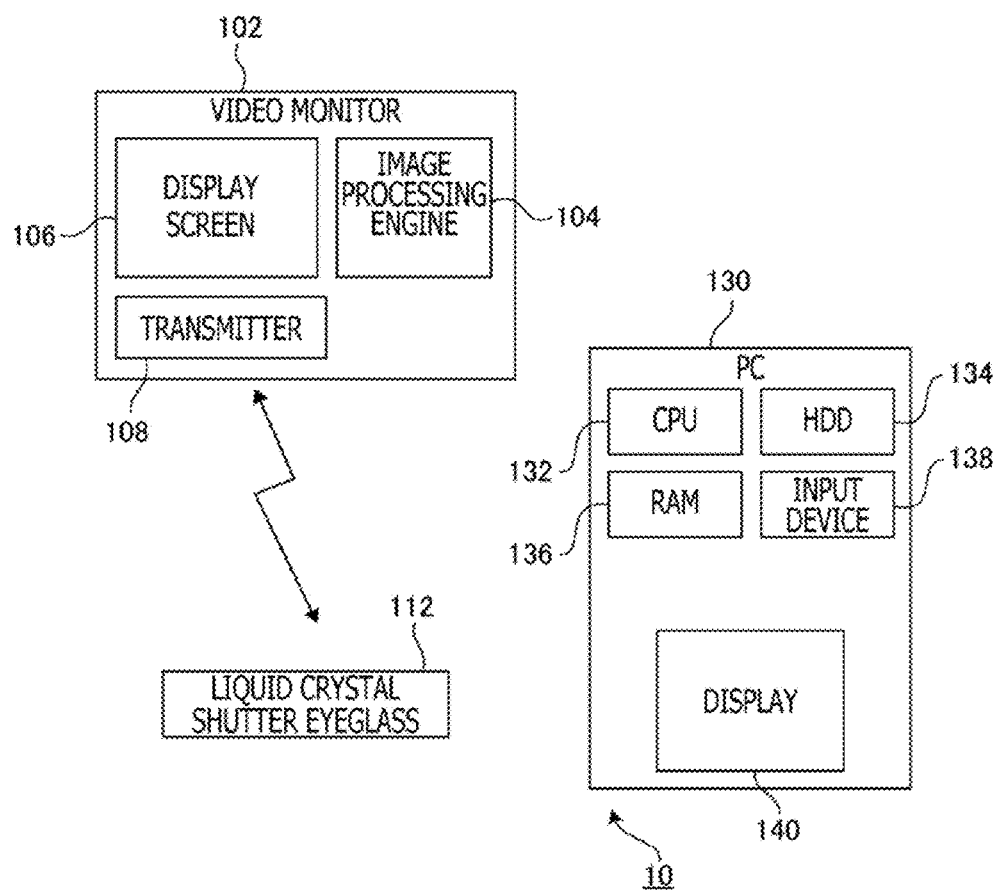
FIG. 2 is a block diagram illustrating a configuration of the eyeglass lens-ordering system according to the embodiment of the invention.

FIG. 1 generally illustrates an eyeglass lens-ordering system 10 according to the embodiment. FIG. 2 is a block diagram illustrating a configuration of the eyeglass lens-ordering system 10. The eyeglass lens-ordering system 10 which is installed, for example, in an eyeglass store is configured to simulate how the outside is viewed when a pair of left and right eyeglass lenses is placed in front of left and right eyes. As shown in FIG. 1, the eyeglass lens-ordering system 10 includes a video monitor 102, and a store computer 130 connected to the video monitor 102.

As shown in FIGS. 1 and 2, the eyeglass lens-ordering system 10 has the video monitor 102. The video monitor 102 is a video monitor (e.g., a liquid crystal display panel TV or a plasma display panel TV) which supports displaying of a three-dimensional image and enables a patient 2 to perform stereoscopic viewing by utilizing binocular parallax. The video monitor 102 uses a flame sequential scheme. An image processing engine 104 of the video monitor 102 generates parallax images for the left and right eyes by processing image data inputted from the store computer 130, and alternately displays the parallax images on a display screen 106 at a high speed.

The patient 2 wears a liquid crystal shutter eyeglass 112 and stands at a reference point, and views the display screen 106 with the head (chin) of the patient 2 being fixed. To the liquid crystal shutter eyeglass 112, a synchronization signal is transmitted from a transmitter 108 mounted on the video monitor 102. The liquid crystal shutter eyeglass 112 controls orientation of liquid crystal in synchronization with the parallax mages displayed on the display screen 106 to alternately block the left and right fields of vision. During a time period where the video monitor 102 is in synchronization with the liquid crystal shutter eyeglass 112, the right eye of the patient 2 views only a right eye virtual image and a left eye of the patient 2 views only a left eye virtual image. The patient 2 perceives, as a three-dimensional object, the parallax images which are displayed on the display screen 106 of the video monitor 103 and are converged at non-corresponding points within Panum's fusional area on retinas.

A displaying format of a three-dimensional image on the video monitor 102 used in the eyeglass lens-ordering system 10 is not limited to the frame sequential scheme. In place of the frame sequential scheme, an anaglyph scheme where a person stereoscopically views parallax images through red and blue color filter eyeglasses or a polarization scheme where a person stereoscopically views, through polarized glasses, parallax images of which polarized conditions are orthogonal to each other may be employed. A so-called naked eye scheme, such as a parallax barrier or a lenticular lens, may be employed.

Basically, the distance (hereafter, referred to as "observation distance od" for convenience of explanation) between the display screen 106 and the eyes of the patient 2 is fixed. However, the observation distance od may be changed for enlarging or reducing the visual field with respect to the virtual mage. Specifically, the video monitor 102 is installed on a seating 122. The seating 122 is configured to be slidable on rails 124. By sliding the seating 122, the observation distance od changes. The changed observation distance od may be directly inputted to the store computer 130 by an operator, or the slid distance of the seating 122 may be detected by a sensor (not shown) and the store computer 130 may employ the detected distance as data. However, the parallax of the virtual images of the left and right eyes need to be changed depending on the observation distance od. That is, it is necessary to produce again the virtual images of the left and right eyes each time the observation distance od is changed.

The store computer 130 is, for example, an ordinary PC (Personal Computer), and includes a CPU (Central Processing Unit) 132, an HDD (Hard Disk Drive) 134, a RAM (Random Access Memory), an input device 138 (keys, as mouse, a game pad and etc.) and a display 140. In the HDD 134, an eyeglasses-wearing simulation program for simulating how the outside is viewed when a pair of left and right eyeglass lenses are placed in front of the left and right eyes.

Figure 3:
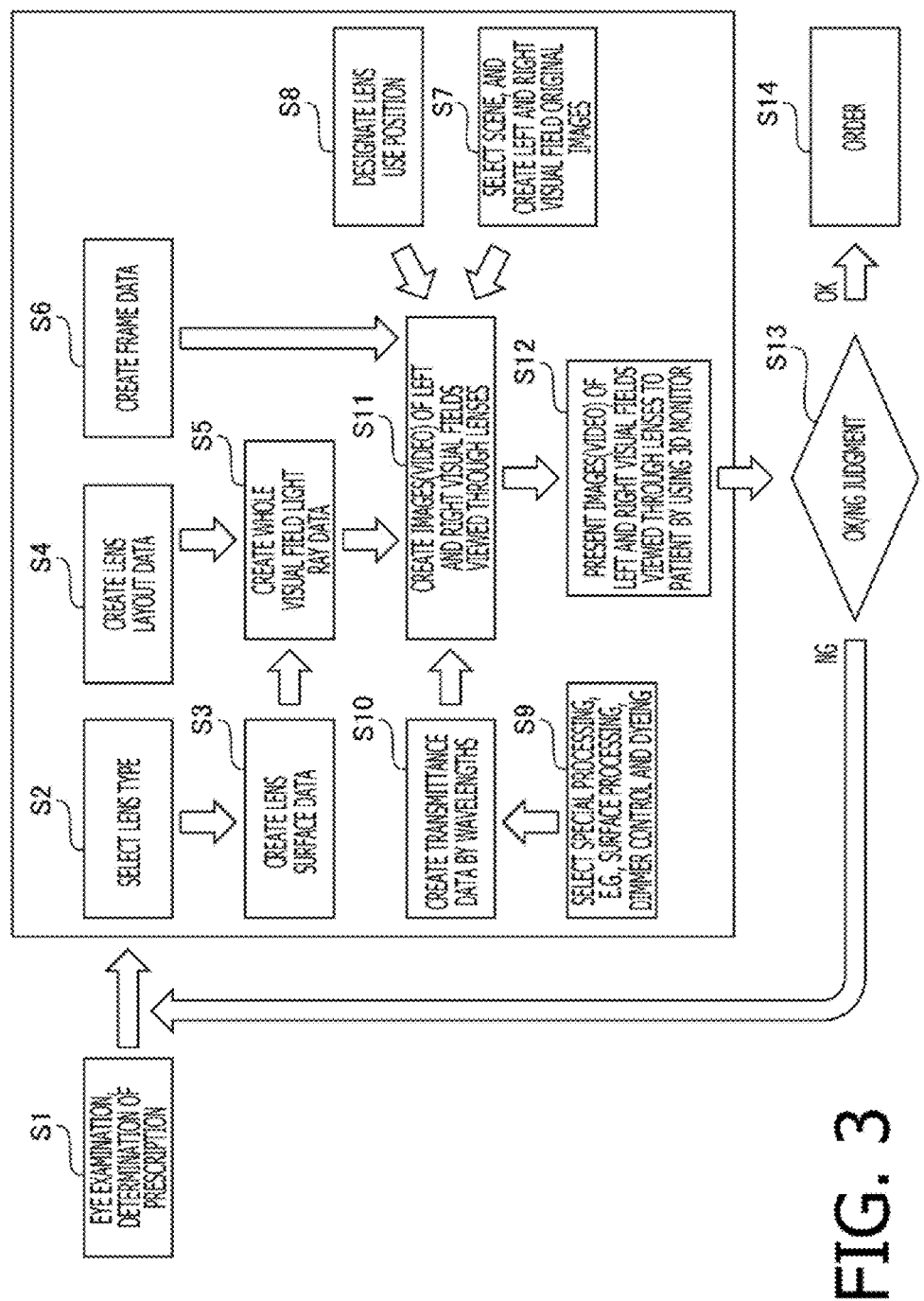
FIG. 3 is an explanatory illustration for explaining a flow of an eyeglasses-wearing simulation by an eyeglasses-wearing simulation program according to the embodiment of the invention.

The CPU 132 starts the eyeglasses-wearing simulation program by loading the eyeglasses-wearing simulation program onto the RAM 136. When the eyeglasses-wearing simulation program is started, a GUI (Graphical User Interface) for inputting various instructions for eyeglasses-wearing simulation is displayed on a display screen of the display 140. FIG. 3 is an explanatory illustration for explaining a flow of the eyeglasses-wearing simulation by the eyeglasses-wearing simulation program.

(Flow of Eyeglasses-Wearing Simulation by Eyeglasses-Wearing Simulation Program)

S1 in FIG. 3 (Eye Examination, Determination of Prescription)

Eye examination is conducted for the patient 2 by an operator who is eyeglass store staff. As a result, a prescription for the patient 2 is determined. The prescription includes spherical power, cylindrical power, cylindrical axis direction, prismatic power, prism base setting, an addition power and distance portion PD (Pupillary Distance) and near portion PD. The operator inputs various prescription data by operating the GUI. Alternatively, data of the various prescription data may be automatically created based on the results of the eye examination.

S2 in FIG. 3 (Selection of Lens Type)

By operating the GUI, the operator selects the type of eyeglass based on the prescription obtained by the eye examination. The selectable eyeglass lenses include, for example, a single-vision spherical lens, a single-vision aspherical lens, a fatigue-relieving lens, a near vision lens dedicated for near vision, a progressive power lens (distance/near vision type, intermediate/near vision type).

S3 in FIG. 2 (Creation of Lens Surface Data)

The eyeglasses-wearing simulation program creates surface shape data so that the prescribed power is achieved by the eyeglass lens of the type selected in step S2 in FIG. 3. The surface shape data may be created, for example, through as known design program. A plurality of types of surface shape data, each of which is uniquely defined by the prescribed power and the type of eyeglass lens, may be prepared in advance in the HDD 134. That is, the eyeglasses-wearing simulation program selects specific surface shape data corresponding to the selected type of eyeglass and the prescribed power, from among data which has been stored in advance, in place of creating surface shape data by the design program. Execution of the design program may be performed, for example, by a server of an eyeglass lens maker connected to the store computer 130 via a network. Furthermore, the specific surface shape data may be stored in the server of the eyeglass lens maker.

S4 in FIG. 3 (Creation of Lens Layout Data)

The operator operates the GUI and inputs layout data corresponding to a request from the patient 2. The layout data includes a position of an eye point, a pantoscopic angle and a tilting angle. When the layout data is not inputted, a default value is used.

S5 in FIG. 33 (Creation of Whole Visual Field Light Ray Data)

When the surface shape data of each of an outer surface and an inner surface of the eyeglass lens, the lens center thickness, a pantoscopic angle, a tilting angle and etc. are determined through the steps of S1 to S4 in FIG. 3, the eyeglasses-wearing simulation program creates the whole visual field light ray data. The whole visual field light ray data is described later.

S6 in FIG. 3 (Creation of Frame Data)

The operator operates the GUI and inputs shape data of the frame selected by the patient 2. The frame data is managed, for example, by a barcode tag, and can be obtained by reading a barcode tag adhered to the frame through use of a barcode reader. When the frame data is not inputted, a default value is used.

S7 in FIG. 3 (Scene Selection and Creation of Original Images of Left and Right Visual Fields)

The operator operates the GUI and selects a desired one scene from among a plurality of three-dimensional virtual scenes prepared in advance. The plurality of three-dimensional virtual scenes are, for example, a scene for a distance vision where distance objects are principally arranged, a scene for a near vision tsar reading books or operating a mobile terminal, and a scene in an office. The three-dimensional virtual scene includes as left eye original image which is an image of virtual objects existing within a pyramid space of a specific visual field defined by placing a rotation center of the left eyeball at a specific position, setting a vertex at the rotation center of the left eyeball and setting a specific visual line direction (a visual line direction of the rotation center of the left eye) as an axis, and a right eye original image which is an image of virtual objects existing within a pyramid space of a specific visual field defined by placing a rotation center of the right eyeball at a position separated by the distance PD from the rotation center of the left eyeball, setting a vertex at the rotation center of the right eyeball and setting an axis extending in the same direction as the visual line direction of the rotation center of the left eye. To the three-dimensional virtual scene, information concerning the distance from each of object points corresponding to all the pixels of the left eye original image to the rotation center of the left eyeball and information concerning the distance from each of object points corresponding to all the pixels of the right eye original image to the rotation center of the right eyeball are attached.

Figure 4A:
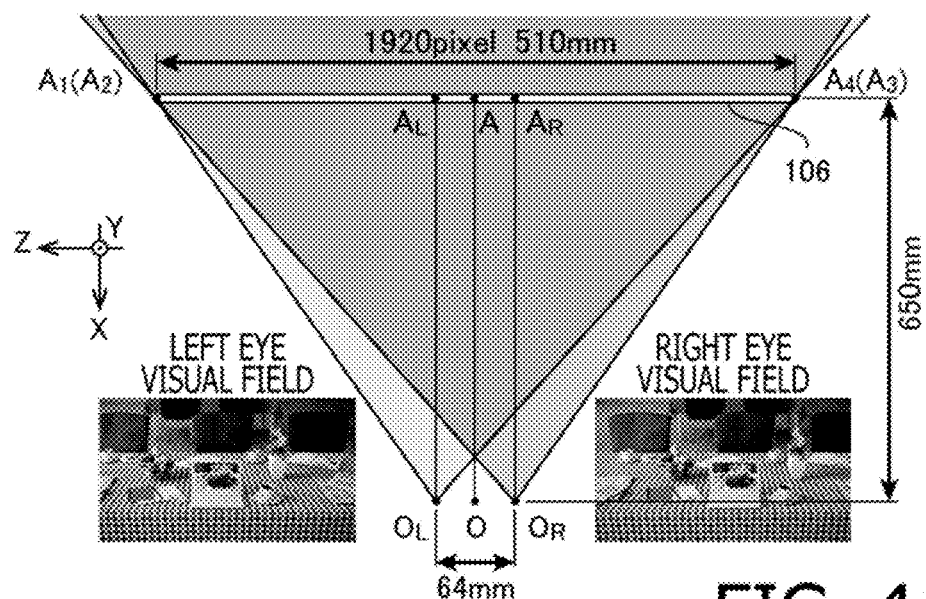
FIGS. 4A and 4B generally illustrate a relationship between a visual field and a display screen for each of an eyeglasses-wearing state and a non-eyeglass-wearing state.
Figure 5A:
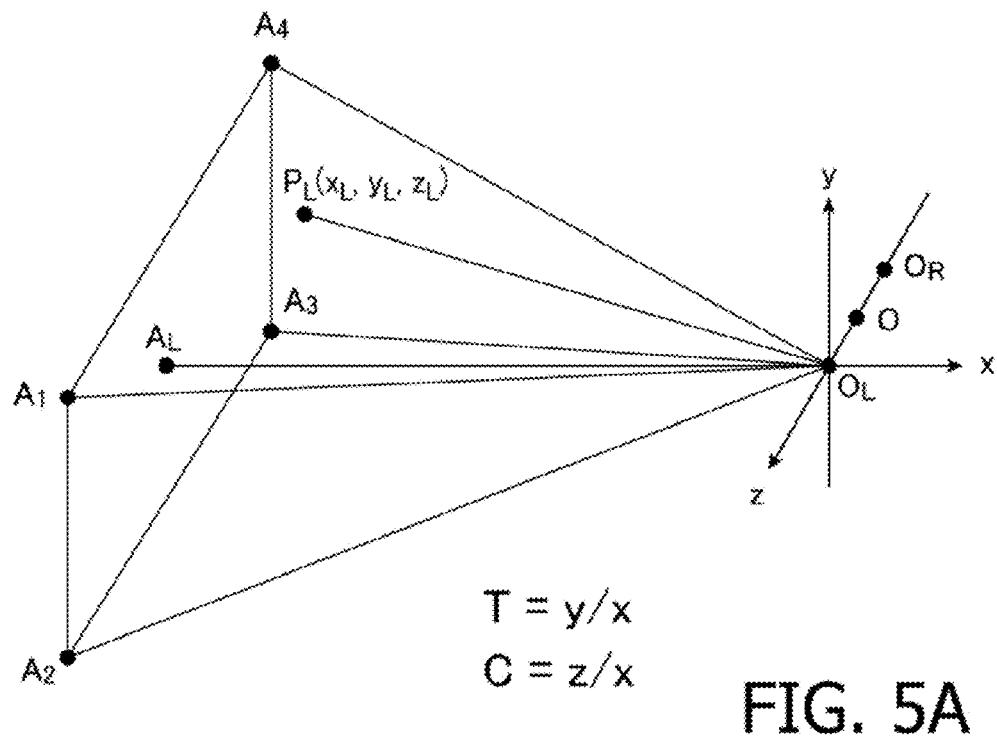
FIGS. 5A and 5B illustrate a coordinate system for left and right visual fields of naked eyes.

FIGS. 4A, 5A and 5C are explanatory illustrations for explaining creation of the original images. In the example shown in FIGS. 4A, 5A and 5B, the depth direction perpendicular to the display screen 106 of the video monitor 102 is defined as x-axis, the up and down direction and the left and right direction which are parallel with the display screen 106 are defined as y-axis and z-axis, respectively. The display screen 106 of the video monitor 102 is a rectangular area (having an aspect ratio of 16:9) surrounded by four apexes $A_1, A_2, A_3$ and $A_4$, and has the size of 510 mm×287 mm and the resolution of 1920 pixel×1080 pixel. Points extending from the left and right eyeball rotation centers $O_L$ and $O_R$ in the x-axis direction and intersecting with the display screen 106 are defined as points $A_L$ and $A_R$, respectively. The observation distance od is the distance OA between the middle point O of the left and right eyeball rotation centers $O_L$ and $O_R$ and the display screen center A of the video monitor 102, and is 650 mm (the distance $O_L A_L$ and the distance $O_R A_R$ are equal to each other, and are 650 mm). Therefore, the visual field becomes 43° (width) by 25° (height). The interval between the left and right eyeball rotation centers $O_L$ and $O_R$ is defined as 64 mm.

The step S7 is further explained with reference to FIGS. 4A, 5A and 5B. First, the eyeglasses-wearing simulation program places virtual objects in is three dimensional virtual space through use of a known computer graphics scheme. The virtual objects constitute the three dimensional virtual scene selected by the patient 2, and are, for example, virtual desk, chair and furniture placed in a virtual room or virtual flowerbed, tree and sign disposed on a virtual field. Thus, the three dimensional virtual scene is created.

As shown in FIG. 5A, the eyeglasses-wearing simulation program places the left eyeball rotation center $O_L$ at a specific position in the three dimensional virtual space. Then, the eyeglasses-wearing simulation program sets, as the visual field, a specific pyramid space $A_1, A_2, A_3$ and $A_4$ defined by setting a vertex at the left eyeball rotation center $O_L$ and setting, as an axis, the left eye visual line $A_L O_L$ parallel with the x-axis, and creates, as the left eye original image, an image of the virtual objects in the visual field. Specifically, in the rectangular coordinate system whose origin is at the left eyeball rotation center $O_L$ and whose x-axis is the left eye visual line $A_L O_L$, a coordinate of an arbitrary object point $P_L(x_L, y_L, z_L)$ in the visual field quadrangular pyramid $A_1, A_2, A_3$ and $A_4$ is represented as T=y/x, C=z/x. T and C are orientation parameters of the object point $P_L(x_L, y_L, z_L)$. By representing each object point in the visual field as this coordinate system, an arbitrary line in the space is viewed as a line on the image. The image where each object point is represented by this coordinate system is defined as the left eye original image. Furthermore, the eyeglasses-wearing simulation program calculates, from the coordinate values, the distance, the object point distance, between the left eye rotation center $O_L$ and each of object points corresponding to pixels of the left eye original image.

Figure 5B:
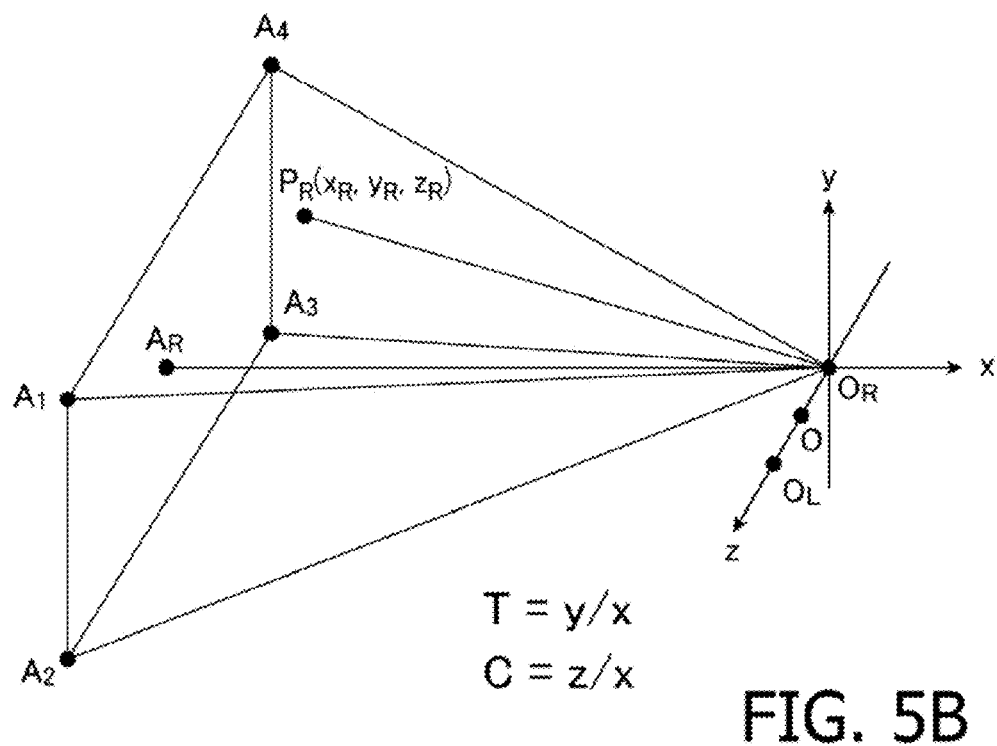

The eyeglasses-wearing simulation program creates the right eye original image through the same manner as that described above, and calculates the object point distance between the right eye rotation center $O_R$ and each of the object points corresponding to pixels of the right eye original image (see FIG. 5B).

With respect a common object point in the three dimensional virtual space, the object point distance and the visual line direction of the left eye are different from those of the right eye because the left and right eyeball rotation centers $O_L$ and $O_R$ are shifted with respect to each other in the z-axis direction. Therefore, the left and right original images, which reflect a common virtual object, have parallax.

In the above described explanation, each original image is created by separately defining the visual filed spaces of the left and right eyes, and the object point distances to the object points corresponding to the pixels are calculated; however, to make the calculation process more efficient, a common visual field space for the left and right eyes may be defined and creation of original images for the left and right eyes and calculation of the object point distances may be performed.

Figure 6A:
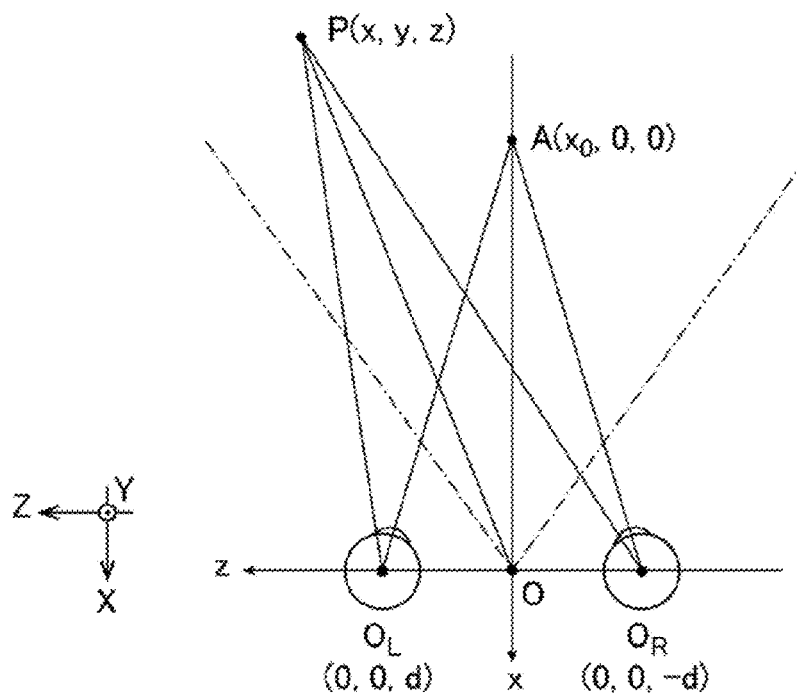
FIGS. 6A and 6B illustrate a coordinate system of visual fields for the eyeglasses-wearing state and the non-eyeglass-wearing state.

The common visual field space for the left and right eyes can be defined by a pyramid having a vertex at the middle point O between the left and right rotation centers $O_L$ and $O_R$ (see FIG. 6A). In this case, the left and right original images and the object point distances to the object points corresponding to the pixels are obtained through calculation by expressions indicated below.

An arbitrary object point P(x, y, z) in the binocular visual field is expressed by the inverse number D of the object point distance OP, the angle ρ formed by the vector PO and the x-axis and the angle of direction θ which are defined by the following expressions. The object point distance is represented by the inverse number for convenience of explanation about the spline function which is described later.

$$D = \frac{1}{\sqrt{x^2 + y^2 + z^2}} \quad \rho = \arccos \frac{-x}{\sqrt{x^2 + y^2 + z^2}} \quad \text{(Expression 1)}$$

$$\theta = \arctan \frac{z}{y}$$

The orientation parameters $T_L$, $C_L$, $T_R$, $C_R$ of each object point of each of the left and right eyes are defined as follows based on the orientation parameters T and C in the binocular visual field. The image where each object point is expressed by the coordinate system of the orientation parameters $T_L$ and $C_L$ is the left eye original image. The image where each object point is expressed by the coordinate system of the orientation parameters $T_R$ and $C_R$ is the right eye original image.

$$T_R = T_L = T = \frac{y}{x} \quad C_L = \frac{z-d}{x} = C - \frac{d}{x} \quad \text{(Expression 2)}$$
$$C_R = \frac{z+d}{x} = C + \frac{d}{x}$$

The inverse number $D_L$ of the object point distance $O_L P$ and the inverse number $D_R$ of the object point distance $O_R P$ are defined as follows.

$$D_L = \frac{1}{\sqrt{x^2 + y^2 + (z-d)^2}} = \quad \text{(Expression 3)}$$
$$\frac{1}{\sqrt{x^2+y^2+z^2}} \frac{1}{\sqrt{1 - \frac{2zd - d^2}{(x^2+y^2+z^2)}}} \approx$$
$$D(1 + (zd - d^2/2)D^2)$$
$$D_R = \frac{1}{\sqrt{x^2 + y^2 + (z+d)^2}} =$$
$$\frac{1}{\sqrt{x^2+y^2+z^2}} \frac{1}{\sqrt{1 + \frac{2zd + d^2}{(x^2+y^2+z^2)}}} \approx$$
$$D(1 - (zd + d^2/2)D^2)$$

S8 in FIG. 3 (Designation of Lens Use Position)

The lens use position means as position at which the visual line to the center of the visual field intersects with the eyeglass lens. Let us consider, for example, the case where the type of eyeglass lens selected in the step S2 in FIG. 3 is a progressive power lens. When the three dimensional virtual scene selected in the step S7 in FIG. 3 is a distance scene which is a part of the whole visual field, the eyeglasses-wearing simulation program designates, as the lens use position, an upper position on the eyeglass lens (e.g., the distance eye point). Furthermore, when the three dimensional virtual scene selected in the step S7 in FIG. 3 is a near scene which is a part of the whole visual field, the eyeglasses-wearing simulation program uses, as the lens use position, a lower position on the eyeglass lens (e.g., the near eye point).

S9 in FIG. 3 (Selection of Special Processing, Such as Surface Processing, Dimmer Control, Dyeing)

The operator operates the GUI and selects presence/absence of the special processing such as of the surface processing, dimmer control, dyeing and etc. The special processing includes dyeing processing, hard coating, anti-reflection coating, ultraviolet light cutting and dimmer control processing.

S10 in FIG. 3 (Creation of Transmittance Data by Wavelengths)

The eyeglasses-wearing simulation program creates transmittance data by wavelengths in accordance with the special processing selected in the step S9 in FIG. 3. By using this data, the eyeglasses-wearing simulation program changes color of the visual field image which is viewed through the eyeglass lens which has been subjected to the special processing.

S11 in FIG. 3 (Creation of the Mages (Video) of the Left and Right Visual Fields which is Viewed Through the Lenses)

Figure 4B:
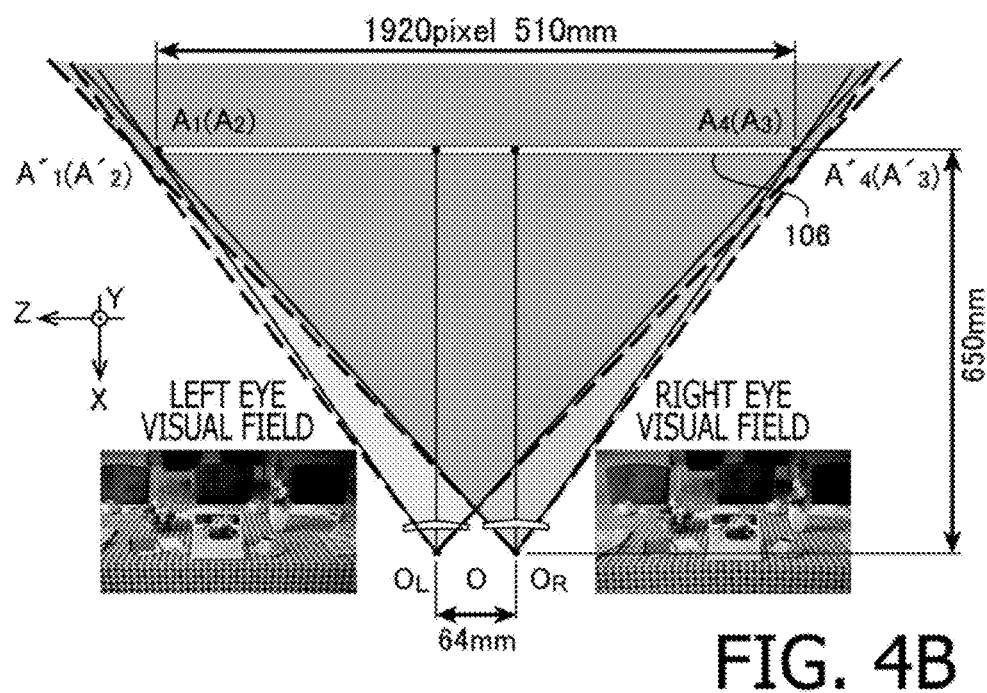

Hereafter, creation of the light ray data of the whole visual field is explained. When the eyeglass lens is worn, the visual field deforms due to the refractive effect by the eyeglass lens and blur occurs. In the example shown in FIG. 4B, the left eye visual field changes from $A_1 O_L A_4$ ($A_2 O_L A_3$) to $A'_1 O_L A'_4 (A'_2 O_L A'_3)$, and the right eye visual field changes from $A_1 O_R A_4$ ($A_2 O_R A_3$) to $A'_1 O_R A'_4 (A'_2 O_R A'_3)$. By wearing the eyeglass lenses, the stereognostic sense of the binocular vision also changes, in addition to change of the distortion and blur of the monocular vision. In particular, since, regarding a progressive power lens, the distribution of the distortion and blur in the visual field is not uniform, the effect to change of the stereognostic sense is large. For this reason, in this embodiment, the light ray data of the whole visual field is created to precisely reflect the distortion and blur caused by the left and right eyes in the visual fields of the left and right eyes.

It takes a large amount of calculation to obtain the distortion and blur by ray tracing for all the pixels of each of the left and right original images while specifying spatial positions. For this reason, in this embodiment, ray tracing is performed only for a limited number of sample points in the whole visual field space, and regarding the distortion and blur between the sample points, values are interpolated through use of known spline interpolation method. The number of sample points is determined appropriately by considering the balance between the amount of calculation and the accuracy of the values of the distortion and blur. Thus, the light ray data of the whole visual field representing the values of the distortion and blur for all the positions in the whole visual field space is created.

Figure 6B:
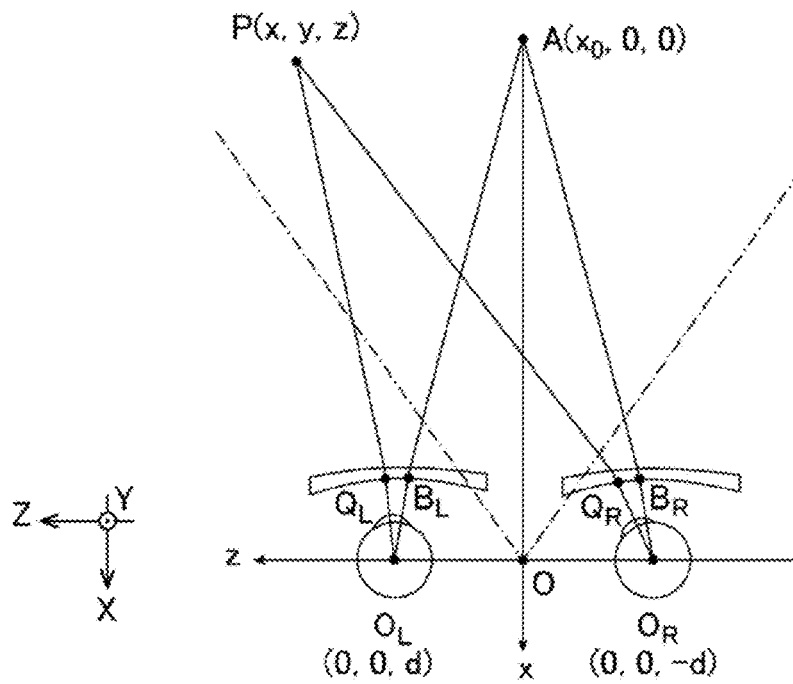

Hereafter, the distortion in the left and right eyes when an object point P is viewed is explained. When the eyeglass lens is placed in front of the eye to have predetermined posture and position (e.g., vertex distance between the corneal apex and the hack vertex of the eyeglass lens, eye point, a pantoscopic angle and a tilting angle), a light ray from an arbitrary object point P reaches the eye while being refracted by the eyeglass lens. The object point P is viewed, from the left and right eyes, as lying on the extension line of the exit light ray $Q_L O_L$ (or $Q_R O_R$) of the eyeglass lens. As shown in FIG. 6B, the fact that the orientation of the exit light ray $Q_L O_L$ (or ($Q_R O_R$) is different from the original light ray $PO_L$ (or $PO_R$) causes the distortion of the visual line.

Figure 7:
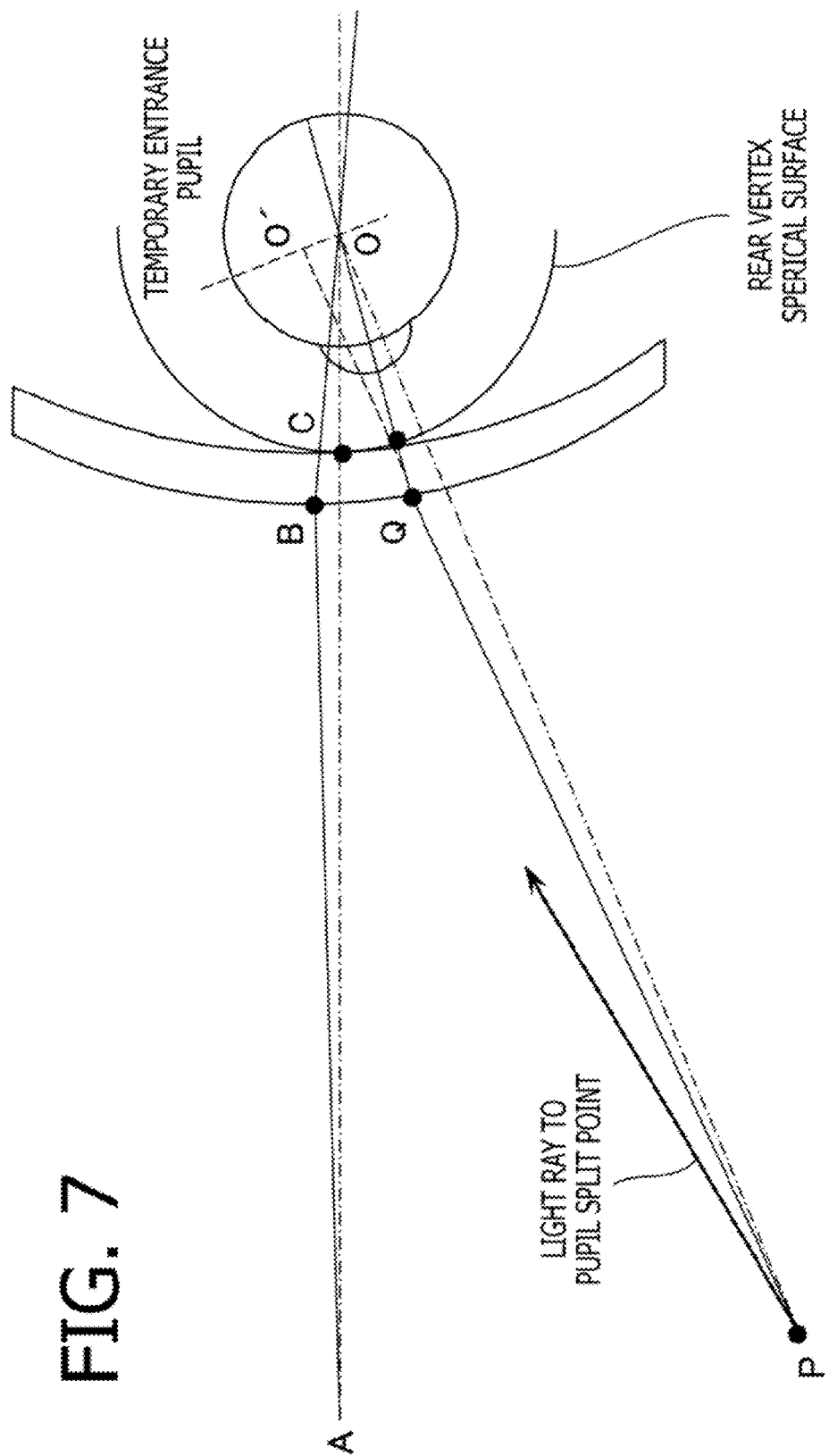
FIG. 7 illustrates an eyeglass lens-eye optical system when an object point is viewed.

Next, the blur in each of the left and right eyes caused when the object point P is viewed is explained. As shown in FIG. 7, the left eye (or the right eye) attempts to capture the object point P on the optical axis by rotating toward the exit light ray $Q_L O_L$ (or $Q_R O_R$). In this case, the amount of accommodation of the eyeball required to cause an image of the object point P to converge on the retina is determined by wavefront power of the light ray radiated from the object point P at the back vertex spherical surface and the correction power for distance vision of the eye. For example, we assume that the correction power for distance vision of the eye is zero. In this case, when the wavefront power at the back vertex spherical surface is −2.0 D (corresponding to a near object at the distance of 0.5 m), the amount of accommodation required for the eye is 2.0 D. It should be noted that the back vertex spherical surface means a spherical surface whose radius is the distance between the rotation center of the eye and the hack vertex of the eyeglass lens and which has the center at the rotation center of the eye.

There is a case where, when the binocular viewing is performed, the powers of the left and right eyes become different from each other depending on passing points of the visual lines on the left and right lenses. Furthermore, frequently, the object point distances of an object at the near distance which is viewed in the peripheral portions of the left and right eyeglass lenses are different between the left and right eyes. In these cases, the amounts of accommodation required for the left and right eyes are different from each other. In the conventional eyeglass-wearing simulation for a single eye, an optimum amount of accommodation where the object point is suitably converged on the retina is set by separately considering the range of eye accommodation for each eye. However, according to the physiological optics, the same amount of accommodation constantly acts on the left and right eyes based on the Hering's law of equal innervations. See, for example, "Introduction to Visual Optics", Alan Tunacliffe, p 319 or "Borish's Clinical Refraction", William J. Benjamin, Second Edition p 162. Therefore, regarding the object point for which different amounts of accommodation are required for the left and right eyes, actually it is impossible to suitably form the images simultaneously on the retinas. However, since, in the conventional eyeglass-wearing simulation for a single eye, constantly the object point which falls within the accommodation range of a single eye is suitably converted on the retina, it was impossible to adequately reproduce the virtual visual field.

For this reason, in this embodiment, in order to realize the more accurate eyeglasses-wearing simulation, the amounts of accommodation of the left and right eyes are determined according to the following rules A and B. Since, as a result, the same amount of accommodation is set for each of the left and right eyes, the condition where the object point is not suitably converged on the retina can be realized, and thereby the blur is reproduced more accurately to comparison with the conventional eyeglass-wearing simulation for a single eye.

(Rule A)

For each of object points in the visual field space, the amount of accommodation by a dominant eye of the patient 2 is defined as the amount of accommodation for the left and right eyes.

(Rule B)

When the dominant eye of the patient 2 is unknown, a smaller one of the required amounts of accommodation for the left and right eyes is defined as the amount of accommodation for the left and right eyes.

Figure 8:
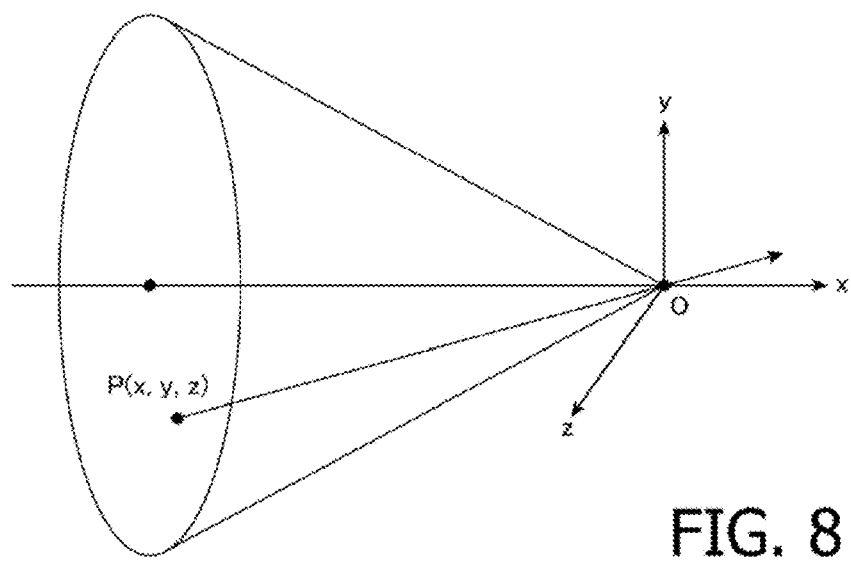
FIG. 8 is an explanatory illustration for explaining a coordinate system of light ray data.

The coordinate system of the light ray data is further explained. As shown in FIG. 8, an arbitrary point P(x, y, z) in the visual field space can be specified by the distance from the rotation center O and the orientation parameters T, C or ρ, θ. The distance PO is represented by the inverse number D, and, for an infinite distance, the inverse number is zero. The orientation parameter Y is a tangent of the vertical angle of direction, and C is a tangent of the horizontal angle of direction. When the vertical/horizontal directions are represented by the polar coordinate, they are the angle of radius ρ and the polar angle of direction θ. These parameters are represented by the following expressions.

$$D = \frac{1}{\sqrt{x^2+y^2+z^2}} \quad T = \frac{y}{x} \quad C = \frac{z}{x} \quad \text{(Expression 4)}$$

-continued
$$\rho = \arctan(\sqrt{T^2+C^2}) \quad \theta = \arctan\frac{C}{T}$$

In the above described expression, T and C are calculated from the coordinate of the object point; however, T and C may be calculated from the direction cosine. Rather, in general, T and C are calculated from the direction cosine. If a unit vector PO is represented by the following expression $$\frac{\vec{PO}}{|\vec{PO}|} = li + mj + nk \quad \text{(Expression 5)}$$

T and C are defined as follows.

$$T = \frac{m}{l} \quad C = \frac{n}{l} \quad \text{(Expression 6)}$$

Thus, an arbitrary point the visual field can be resented (D, T, C) or (D, ρ, θ) in addition to the coordinate (x, y, z). In the case where the point is represented by (x, y, z), if the domains of x, y, z are defined, the space is partitioned by a parallelepiped. On the other hand, in the case where the point is represented by (D, T, C), if domains of D, T, C are defined, the space is partition by a quadrangular pyramid. In the patent document 1, the space is defined by the scheme using this quadrangular pyramid. In the case where the space is represented by (D, ρ, θ), if domains of D, ρ, θ are defined, the space is partitioned by a circular cone (θ becomes 0-360). Since in general an eyeglass lens has a circular shape, representation by (D, ρ, θ) is convenient.

The substance of the light ray data of the whole visual field is coefficients of the spline function for calculating the distortion and blur for an arbitrary object point. An example of the light ray data of the whole visual field is here presented. For creating the light ray data of the whole visual field, the visual field space is represented by the pyramid of FIG. 6, and a sample pint is set by each coordinate axis. For example, the sample point of the inverse number D of the object point distance is defined as (0.0, 0.5, 1.0, 1.5, ... 3.5). 0.0 D is the infinity. For example, 3.5 D is approximately equal to 286 mm. The sample points are not required to have constant intervals. The sample point of the angle of radius ρ is, for example, (0.0, 1.0, 2.0, ... 60) degrees. Regarding the angle of direction θ, the sample point is set so that 0 to 30° is covered. The eyeglasses-wearing simulation program performs ray tracing of binocular vision for all the intersection points of the sample points with respect to the axes, and calculates the data of the distortion and blur for each intersection point. The eyeglasses-wearing simulation program derives the spline coefficients, which are the substance of the light ray data of the whole visual field, by using the calculation results of the distortion and blur at each intersection point, and stores the coefficients in a storage area e.g., the HDD 134.

For example, the vertical orientation parameter $T_R'$ of the right eye is represented by the following expression by defining $N_i$, $N_j$, $N_k$ as the B-spline basis function, defining the coordinate of each target point included in the right eye visual field as (D, ρ, θ), and defining $C_{jki}$ as the coefficient of the basis function near each target point. The position of a node (substituted by the sample point) near each target point (D, ρ, θ) is defined depending on the interval of the nodes.

$$T'_R = T'_R(D, \rho, \theta) = \sum_{i,j,k} C_{i,j,k} N_i(D) N_j(\rho) N_k(\theta) \quad \text{(Expression 7)}$$

Other parameters, such as the image side horizontal orientation parameter $C_R'$ or the calculated eyesight representing the degree of blur can also be obtained through the similar manner.

The eyeglasses-wearing simulation program creates the left and right visual field images which are viewed through the left and right lenses based on the various data including the light ray data of the whole visual field created in the step S5 of FIG. 3, the frame data created in the step S6 of FIG. 3, left and right original image data created in the step S7 of FIG. 3, the lens use position designated in the step S8 of FIG. 3 and the transmittance data by wavelengths created in the step S10 of FIG. 3. Specifically, based on the light ray data (the coefficients of the spline function) of the whole visual field created in the step S5 of FIG. 3, the eyeglasses-wearing simulation program defines, as a post-transmission left lens visual field, the left eye visual field whose center corresponds to the direction from the left eye rotation center to the lens use position of the left eye (designated in the step S8 of FIG. 3), and creates the image of the visual field which is viewed through the left eye eyeglass lens to which the distortion and the blur by the eyeglass lens is applied, by applying the value of the distortion and the blur corresponding to the object point distance to the object point corresponding to each pixel of the left eye original image in the post-transmission left lens visual field. The eyeglasses-wearing simulation program also creates the image of the visual field which is viewed through the right eye eyeglass through us of the similar manner. Furthermore, the eyeglasses-wearing simulation program changes color of the left and right parallax images based on the transmittance data by wavelengths. To an area of the original image corresponding to the visual field of the outside of the frame, the distortion is not added, and blur for naked eye is additionally created and added.

The processes for creating the data similar to the light ray data of the whole visual field and adding the distortion and blur by applying the created data to the original image (e.g., a distorted original image creation process, a PSF (Point Spread Function) obtaining process, a convolution process, etc.) are explained, for example, in the patent document 1 and Japanese Patent Publication Nos. JP3825654 (B2) and JP3919097 (B2).

S12 in FIG. 3 (Presentation of the Images of the Left and Right Visual Fields Viewed Through Lenses to the Patient, Through Use of a 3D Monitor)

The eyeglasses-wearing simulation program transmits, to the video monitor 102, the image data of the left and right visual fields which are viewed through lenses created in the step S11 of FIG. 3 to present the image of the image data to the patient 2 by displaying the image of the image data on the display screen 106. According to the embodiment, when the value of the blur of each object point is calculated, the common amount of accommodation is set for each of the left and right eyes according to the predetermined rule, without setting optimum amounts of accommodation for the left and right eyes. For this reason, the patient 2 is given the eyeglasses-wearing simulation reflecting more accurately how the outside is viewed in the state of binocular vision when the eyeglasses are worn, and is able to achieve the stereoscopic viewing for the parallax images in a feeling close to the reality.

On the image of each of the left and right visual fields, a position of a fitting cross (a point on the lens centered at the pupil) of the eyeglass lens may be superimposed. By superimposing the position of the fitting cross, it becomes possible to simulate appearance of the outside when the fitting cross shifts from an original point (e.g., a state where framing is not conducted properly). The operator is able to quantitatively recognize the tolerance for the shift of the framing by visually recognizing change of the appearance of the outside and the shift amount of the position of the fitting cross.

S13 in FIG. 3 (OK/NG Judgment)

For example, when a lens targeted for the simulation is a progressive power lens, the patient 2 selects, depending on the purpose, sequentially a plurality of three dimensional virtual scenes, such as a scene for distance vision, a scene for near vision, and a scene for intermediate distance vision, and visually recognizes images viewed through eyeglass lenses. Then, if the patient 2 has an uncomfortable feeling with respect to at least one of the scenes, the operator inputs a command for redesign to the store computer 130, to change the lens design. That is, the eyeglasses-wearing simulation program executes again the steps from S2 in FIG. 3. The steps S2 to S13 in FIG. 3 are repeatedly executed, for example, until the patient 2 has a comfortable feeling to images of the visual fields of all of the three dimensional scenes which are viewed through lenses.

S14 in FIG. 3 (Order)

When the patient 2 has a comfortable feeling for all the selected three dimensional scenes by visually recognizing the images of the left and right visual fields viewed through lenses, the operator inputs a common for ordering the eyeglass lenses to the store computer 130. The eyeglasses-wearing simulation program transmits at least one of the current prescription data used for creating the images of the left and right visual fields viewed through lenses and the design data of the eyeglass lenses, to an eyeglass lens manufacturing factory 20. The design data of the eyeglass lens as used herein means design data of a pair of eyeglass lenses created by the eyeglasses-wearing simulation program based on the above described prescription data.

(Eyeglass Lens Manufacturing Factory and Eyeglass Lens Manufacturing Method)

Figure 9:
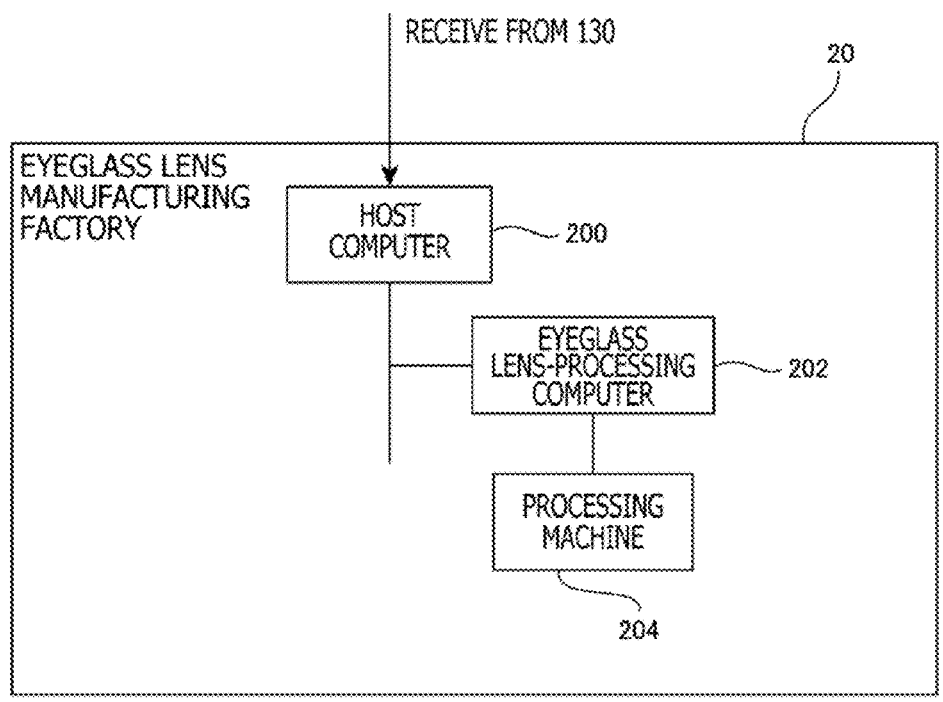
FIG. 9 is a block diagram illustrating an eyeglass lens manufacturing factory for implementing an eyeglass lens manufacturing method according to the embodiment of the invention.
Figure 10:
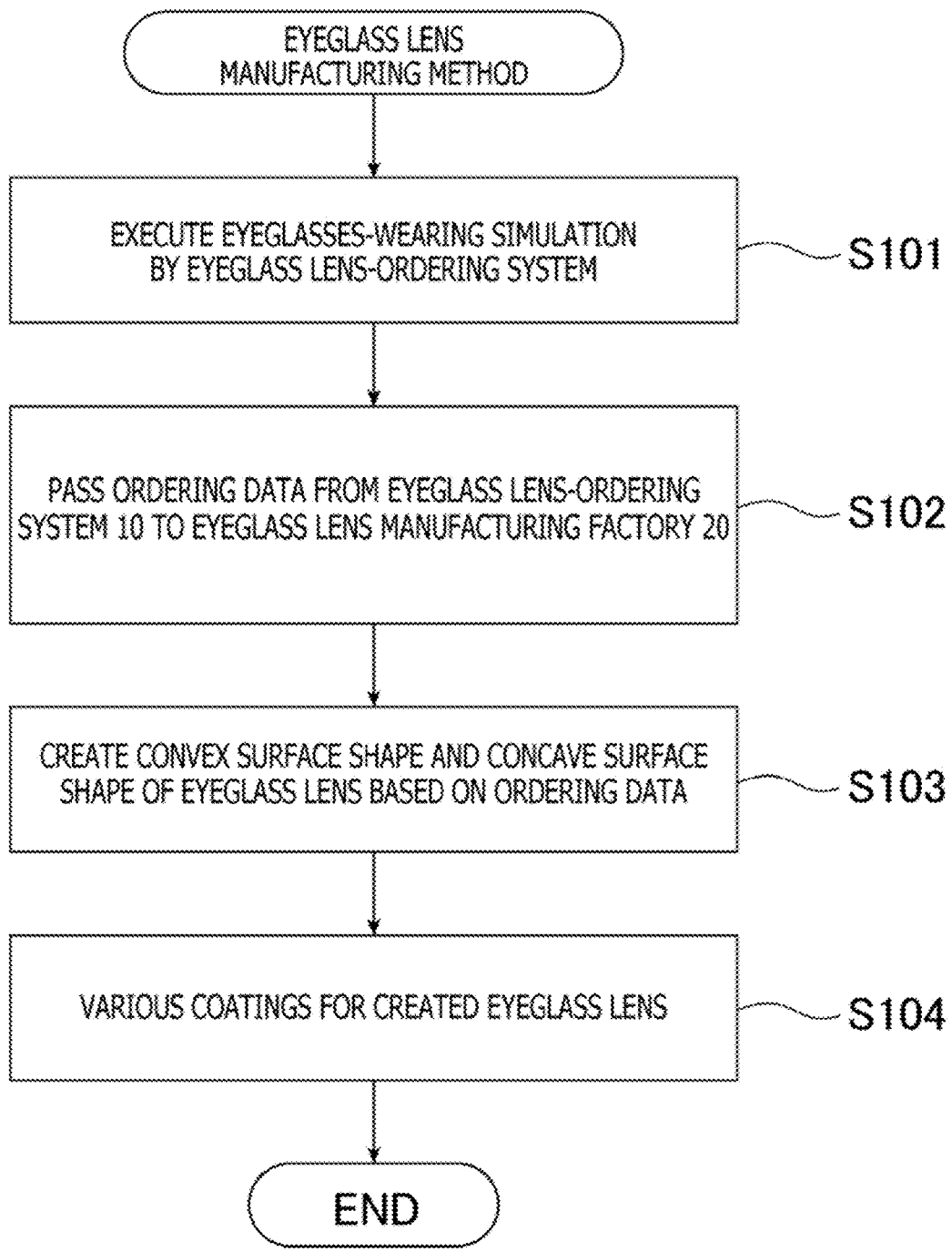
FIG. 10 is a flowchart illustrating the eyeglass lens manufacturing method according to the embodiment of the invention.

FIG. 9 is a block diagram illustrating the eyeglass lens manufacturing factory 20 in which the eyeglass lens manufacturing method according to the embodiment of the invention is implemented. FIG. 10 is a flowchart illustrating the eyeglass lens manufacturing method according to the embodiment of the invention. As shown in FIG. 9, in the eyeglass lens manufacturing factory 20, a LAN (Local Area Network) hosted by a host computer 200 is constructed, and various terminal devices (not shown) are connected thereto.

The host computer 200 receives the ordering data obtained by execution of the eyeglasses-wearing simulation program (S101 in FIG. 10, FIG. 10) by the eyeglass lens-ordering system 10 from the store computer 130, and transfers the ordering data to an eyeglass lens-processing computer 202 (S102 in FIG. 10).

The eyeglass lens-processing computer 202 is a general PC in which an eyeglass lens-processing program is installed. The operator sets the lens base material on a processing machine (a cutting machine such as a curve generator) 204, and inputs a command for starting the processing to the eyeglass lens-processing computer 202. The eyeglass lens-processing computer 202 drives and controls the processing machine 204 to process the lens base material based on the ordering data (the received prescription data or the design data of the eyeglass lens) transferred from the host computer 200, and thereby creates a convex surface shape and a concave surface shape of the eyeglass lens (S103 in FIG. 10). Various coatings such as a hard coat film, an antireflection film or an UV cutting film, are applied to the eyeglass lens whose each surface has been created (S104 in FIG. 10). As a result, the eyeglasses are completed and are delivered to an eyeglass store. Specifically, when the eyeglass lens is simulated by applying the above described rule A, both of the pair of left and right eyeglass lenses is given the amount of accommodation of a single vision of the dominant eye of the patient 2 and the value of blur is calculated. On the other hand, when the eyeglass lens is simulated by applying the above described rule B, both of the pair of left and right eyeglass lenses is given the amount of accommodation which is a smaller amount of amounts of accommodations required for the left and right eyes, and the value of blur is calculated.

The foregoing is the explanation about the embodiment of the invention. The invention is not limited to the above described configuration, and can be varied in various ways within the technical scope of the invention. For example, in this embodiment the video monitor 102 and the store computer 130 are provided as separate devices; however, in another embodiment, the video monitor 102 and the store computer 130 may be integrally provided as one device.

Furthermore, in this embodiment, the explanation focuses on a still image; however, by creating a number of time-series still images by changing the positions of the left and right eyeball rotation centers and the center visual line directions and by continuously reproducing the plurality of still images, a moving image may be simulated.

In the above described embodiment, the pair of e eyeglass lenses are designed by creating and displaying the simulation images to enable the patient 2 to simulate the wearing state; however, in another embodiment, the pair of eyeglass lenses may be designed by focusing on an amount of accommodation for a single vision of the dominant eye of the patient 2 or a smaller one of amounts of accommodation required for the left and right eyes, without creating and displaying the simulation image. That is, when the pair of eyeglass lenses are designed based on the patient's prescription, the value of blur which the eyeglass lens should have may be calculated by setting the same amount of accommodation to the left and right eyes in regard to all the object points in the virtual Visual field spaces of the left and right eyes (i.e., setting an amount of accommodation of a single vision of the dominant eye of the patient as the amount of accommodation for each of the left and right eyes or setting a smaller one of amounts of accommodation required for the left and right eyes as an amount of accommodation for each of the left and right eyes), and then the pair of eyeglass lenses may be designed using the calculated value of blur. Thus, even the pair of eyeglass lenses designed without executing the wearing simulation can also be manufactured by the eyeglass lens manufacturing factory 20 as in the case of the above described embodiment.

In the foregoing explanation, the pair of eyeglass lenses are manufactured in the eyeglass lens manufacturing factory 20 based on the deign results. On the other hand, there is a case where lenses having substantially the same performance as the designed pair of eyeglass lenses have already been provided (provided as a pair of lenses or provided as separate lenses for left and right eyes). In such a case, appropriate eyeglass lenses according to the design results may be selected from the existing lenses for each of the left and right eyes so that a pair of eyeglass lenses is obtained.

What is claimed is:

1. An eyeglasses-wearing simulation method for simulating how an outside is viewed when a pair of left and right eyeglass lenses are placed in front of left and right eyes, the method comprising:

creating a pair of left and right original parallax images based on virtual scene data selected by a patient constituted by virtual objects placed in visual field spaces of the left and right eyes, and configured to enable a patient to perform stereoscopic viewing by utilizing binocular parallax;

calculating, based on optical data of a right eye eyeglass lens of the pair of left and right eyeglass lenses designed in accordance with prescription information of the patient, distortion and blur of the right eye eyeglass lens and processing the right eye original parallax image by adding the distortion and blur of the right eye eyeglass lens to the right eye original parallax image, and calculating, based on optical data of a left eye eyeglass lens of the pair of left and right eyeglass lenses, distortion and blur of the left eye eyeglass lens and processing the left eye original parallax image by adding the distortion and blur of the left eye eyeglass lens to the left eye original parallax image, so as to create images of left and right visual fields viewed through the pair of left and right eyeglass lenses; and stereoscopically displaying the processed images viewed through the pair of left and right eyeglass lenses on a screen, wherein, a value of the blur is calculated by setting a same amount of accommodation to the left and right eyes in regard to all object points in the visual field spaces.

2. The eyeglasses-wearing simulation method according to claim 1, wherein the same amount of accommodation is one of:

A: an amount of accommodation in a single vision of a dominant eye of the patient, for each object point in the visual field spaces; and B: a smaller one of amounts of accommodation required for the left and right eyes, for each object point in the visual field spaces.

3. A non-transitory computer readable medium having computer readable instruction stored thereon, which, when executed by a processor of a computer, configures the processor to perform the steps of:

creating a pair of left and right original parallax images based on virtual scene data selected by a patient constituted by virtual objects placed in visual field spaces of the left and right eyes, and configured to enable a patient to perform stereoscopic viewing by utilizing binocular parallax;

calculating, based on optical data of a right eye eyeglass lens of the pair of left and right eyeglass lenses designed in accordance with prescription information of the patient, distortion and blur of the right eye eyeglass lens and processing the right eye original parallax image by adding the distortion and blur of the right eye eyeglass lens to the right eye original parallax image, and calculating, based on optical data of a left eye eyeglass lens of the pair of left and right eyeglass lenses, distortion and blur of the left eye eyeglass lens and processing the left eye original parallax image by adding the distortion and blur of the left eye eyeglass lens to the left eye parallax original image, so as to create images of left and right visual fields viewed through the pair of left and right eyeglass lenses; and stereoscopically displaying the processed images viewed through the pair of left and right eyeglass lenses on a screen, wherein, a value of the blur is calculated by setting a same amount of accommodation to the left and right eyes in regard to all object points in the visual field spaces.

4. The non-transitory computer readable medium according to claim 3, wherein the same amount of accommodation is one of:

A: an amount of accommodation in a single vision of a dominant eye of the patient, for each object point in the visual field spaces; and B: a smaller one of amounts of accommodation required for the left and right eyes, for each object point in the visual field spaces.

5. An eyeglasses-wearing simulation device for simulating how an outside is viewed when a pair of left and right eyeglass lenses is placed in front of left and right eyes, comprising:

an original image creation unit configured to create a pair of left and right original parallax images based on virtual scene data selected by a patient constituted by virtual objects placed in visual field spaces of the left and right eyes, and configured to enable a patient to perform stereoscopic viewing by utilizing binocular parallax;

an image calculation unit configured to calculate, based on optical data of a right eye eyeglass lens of the pair of left and right eyeglass lenses designed in accordance with prescription information of the patient, distortion and blur of the right eye eyeglass lens and to process the right eye original parallax image by adding the distortion and blur of the right eye eyeglass lens to the right eye original parallax image, and configured to calculate, based on optical data of a left eye eyeglass lens of the pair of left and right eyeglass lenses, distortion and blur of the left eye eyeglass lens and to process the left eye original parallax image by adding the distortion and blur of the left eye eyeglass lens to the left eye original parallax image, so as to create images of left and right visual fields viewed through the pair of left and right eyeglass lenses; and an image display unit configured to stereoscopically display the processed images viewed through the pair of left and right eyeglass lenses, wherein, in the image calculation unit, a value of the blur is calculated by setting a same amount of accommodation to the left and right eyes in regard to all object points in the visual field spaces.

6. The eyeglasses-wearing simulation device according to claim 5, wherein the same amount of accommodation is one of:

A: an amount of accommodation in a single vision of a dominant eye of the patient, for each object point in the visual field spaces; and B: a smaller one of amounts of accommodation required for the left and right eyes, for each object point in the visual field spaces.

7. An eyeglass lens-ordering system for ordering a pair of eyeglass lenses using an eyeglasses-wearing simulation device for simulating how an outside is viewed when the pair of left and right eyeglass lenses is placed in front of left and right eyes, comprising:

an eyeglasses-wearing simulation device according to claim 5; and an order data transmission unit configured to transmit, as ordering data, one of the prescription information used by the image creation unit of the eyeglasses-wearing simulation device and eyeglass lens pair data designed based on the prescription data, to a predetermined ordering destination.

8. An eyeglass lens manufacturing method, comprising the steps of:

executing an eyeglasses-wearing simulation method according to claim 1;

transmitting, as ordering data, one of the prescription information used in the image creation step in the eyeglasses-wearing simulation method and eyeglass lens pair data designed based on the prescription information, to a predetermined ordering destination; and processing lens material by driving and controlling a processing machine based on one of the transmitted prescription data and the transmitted eyeglass lens pair data designed based on the prescription information, thereby manufacturing the eyeglass lenses.

9. The eyeglasses-wearing simulation method according to claim 1, wherein object points of the left eye original parallax image are represented by a coordinate system having an origin at a left eyeball rotation center, and object points of the right eye original parallax image are represented by a coordinate system having an origin at a right eyeball rotation center.

10. The eyeglasses-wearing simulation method according to claim 9, further comprising:

calculating, from coordinate values, an object point distance between the left eye rotation center and each of the objects points corresponding to pixels of the left eye original parallax image, and calculating, from coordinate values, an object point distance between the right eye rotation center and each of the objects points corresponding to pixels of the right eye original parallax image.

11. The non-transitory computer readable medium according to claim 3, wherein object points of the left eye original parallax image are represented by a coordinate system having an origin at a left eyeball rotation center, and object points of the right eye original parallax image are represented by a coordinate system having an origin at a right eyeball rotation center.

12. The non-transitory computer readable medium according to claim 11, wherein the steps further comprise:

calculating, from coordinate values, an object point distance between the left eye rotation center and each of the objects points corresponding to pixels of the left eye original parallax image, and calculating, from coordinate values, an object point distance between the right eye rotation center and each of the objects points corresponding to pixels of the right eye original parallax image.

13. The eyeglasses-wearing simulation device according to claim 5, wherein object points of the left eye original parallax image are represented by a coordinate system having an origin at a left eyeball rotation center, and object points of the right eye original parallax image are represented by a coordinate system having an origin at a right eyeball rotation center.

14. The eyeglasses-wearing simulation device according to claim 13, wherein the original image creation unit is further configured to:
- calculate, from coordinate values, an object point distance between the left eye rotation center and each of the objects points corresponding to pixels of the left eye original parallax image, and
- calculate, from coordinate values, an object point distance between the right eye rotation center and each of the objects points corresponding to pixels of the right eye original parallax image.

* * * * *